US010034603B2

United States Patent
Matsuo et al.

(10) Patent No.: US 10,034,603 B2
(45) Date of Patent: Jul. 31, 2018

(54) ENDOSCOPE CONDUIT SWITCHING APPARATUS

(71) Applicant: OLYMPUS CORPORATION, Tokyo (JP)

(72) Inventors: Naomi Matsuo, Hachioji (JP); Suguru Okaniwa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/266,725

(22) Filed: Sep. 15, 2016

(65) Prior Publication Data

US 2017/0000323 A1 Jan. 5, 2017

Related U.S. Application Data

(63) Continuation of application No. PCT/JP2015/061629, filed on Apr. 15, 2015.

(30) Foreign Application Priority Data

Aug. 7, 2014 (JP) ................................. 2014-161448

(51) Int. Cl.
*A61B 1/00* (2006.01)
*A61B 1/12* (2006.01)
(Continued)

(52) U.S. Cl.
CPC ................ *A61B 1/126* (2013.01); *A61B 1/00* (2013.01); *A61B 1/015* (2013.01); *G02B 23/24* (2013.01);
(Continued)

(58) Field of Classification Search
CPC ........... A61B 1/12; A61B 1/126; A61B 1/015; A61B 1/00068; G02B 23/24; G02B 23/2476; G02B 27/0006
See application file for complete search history.

(56) References Cited

U.S. PATENT DOCUMENTS

| 5,027,791 A | 7/1991 | Takahashi |
| 2003/0181787 A1 | 9/2003 | Kondo |

FOREIGN PATENT DOCUMENTS

| JP | 2-159244 | 6/1990 |
| JP | 2-168927 | 6/1990 |
| JP | 3651982 | 3/2005 |

OTHER PUBLICATIONS

International Search Report dated Jul. 7, 2015 received in International Application No. PCT/JP2015/061629, together with an English-language translation.

(Continued)

*Primary Examiner* — Timothy J Neal
(74) *Attorney, Agent, or Firm* — Scully, Scott, Murphy & Presser, P.C.

(57) ABSTRACT

An endoscope conduit switching apparatus configured to have a cylinder to which a plurality of conduits provided in an endoscope are connected, a piston that is fitted and inserted into the cylinder to be capable of advancing and retreating, and an urging member that urges the piston to the normal position, and switch communication states of the plurality of conduits, includes: a seal member configured to isolate the gas flow conduit from an outside, when the piston is in the normal position, and a leak portion configured to be provided on the wall face of the other one, and open the gas flow conduit to the outside in a space between the cylinder and the piston when the piston is in a position that closes the liquid flow conduit and allows the gas flow conduit to be continuous.

3 Claims, 5 Drawing Sheets

(51) Int. Cl.
G02B 23/24 (2006.01)
A61B 1/015 (2006.01)
G02B 27/00 (2006.01)

(52) U.S. Cl.
CPC ..... *G02B 23/2476* (2013.01); *G02B 27/0006* (2013.01)

(56) References Cited

OTHER PUBLICATIONS

Japanese Notification of Reasons for Rejection dated Mar. 1, 2016 received from Japanese Patent Application No. 2015-558045, together with an English-language translation and statement.
Extended Supplementary European Search Report dated Nov. 23, 2017 in European Patent Application No. 15 82 95691.

ENDOSCOPE CONDUIT SWITCHING APPARATUS

CROSS REFERENCE TO RELATED APPLICATION

This application is a continuation application of PCT/JP2015/061629 filed on Apr. 15, 2015 and claims benefit of Japanese Application No. 2014-161448 filed in Japan on Aug. 7, 2014, the entire contents of which are incorporated herein by this reference.

BACKGROUND OF THE INVENTION

1. Field of the Invention

The present invention relates to an endoscope conduit switching apparatus for performing conduit switching of air/water feeding fluid conduits in an endoscope.

2. Description of the Related Art

Conventionally, endoscopes that are configured by having insertion portions formed into elongated shapes have been widely used in the medical field, the industrial field and the like. Of the endoscopes, a medical endoscope which is used in the medical field is configured to be capable of observing an organ in a body cavity by an elongated insertion portion being inserted into a body cavity which is a subject, and applying various treatments by using a treatment instrument inserted into a treatment instrument insertion channel which is included in the endoscope in accordance with necessity. An industrial endoscope which is used in the industrial field is configured to be capable of performing observation and inspection of a state of an inside of an object, for example, scratches, and corrosion by an elongated insertion portion being inserted into an inside of an object, for example, a jet engine or a plant piping.

In a conventional endoscope as above, an observation window and an illumination window are provided on a distal end face of the insertion portion, and the conventional endoscope is configured so that the inside of a body cavity which is an object to be observed can be observed via the observation window, and illuminating light can be emitted to the inside of the body cavity which is the object to be observed through the illumination window.

Further, in the conventional endoscopes of the configurations as above, especially in the medical endoscopes, body fluids or the like adhere to outer surfaces of the observation windows and hinder observation during use of the endoscopes. For this reason, some of the conventional endoscopes each have an air/water feeding mechanism for feeding a fluid such as water for cleaning the outer surface of the above described observation window toward the outer surface of the observation window, and thereafter feeding gas such as air for drying a lens surface toward the outer surface of the observation window.

The above described air/water feeding mechanism in the endoscope is configured by an air/water feeding nozzle which is provided in the vicinity of the above described observation window and the like on the distal end face of the endoscope insertion portion, a fluid conduit which is inserted and disposed in the insertion portion and an operation portion of the endoscope and is for connecting the above described air/water feeding nozzle and a predetermined air/water feeding apparatus, an operation member which is provided at the operation portion, a conduit switching apparatus which is provided in the operation portion and performs switching of air feeding and water feeding, and the like.

The above described fluid conduit includes a plurality of tubes such as an air feeding tube and a water feeding tube which are formed of flexible tubes, for example. The above described air feeding tube and the above described water feeding tube have respective one ends connected to the air/water feeding apparatus, and have the other ends connected to the conduit switching apparatus. From the conduit switching apparatus, the air feeding tube and the water feeding tube are extended into the insertion portion, and the air feeding tube and the water feeding tube join each other in the insertion portion via a branch tube to be connected to the air/water feeding nozzle thereafter.

By the configuration as above, a cleaning liquid such as water and pressurized air or the like are configured to be able to be properly injected toward the outer surface of the observation window by performing switching of air feeding and water feeding in the above described conduit switching apparatus.

As endoscope conduit switching apparatuses of this kind, endoscope conduit switching apparatuses of various modes have been conventionally proposed by Japanese Patent No. 3651982 and the like, and have been put into practical use.

The endoscope conduit switching apparatuses disclosed by Japanese Patent No. 3651982 described above and the like each have a cylinder to which a plurality of conduits (an air feeding tube, a water feeding tube and the like) provided in the endoscope are connected, and a piston which is fitted to be capable of advancing and retreating in the cylinder, and has a configuration of switching a communication state of the plurality of conduits by an operator.

SUMMARY OF THE INVENTION

An endoscope conduit switching apparatus of one aspect of the present invention is an endoscope conduit switching apparatus configured to have a cylinder to which a plurality of conduits provided in an endoscope and including a gas flow conduit and a liquid flow conduit are connected, a piston that is fitted and inserted into the cylinder to be capable of advancing and retreating, and is moved between a normal position and a pushed-in position where the piston is pushed inward of the cylinder from the normal position, and an urging member that urges the piston toward the normal position, and switch communication states of the plurality of conduits so as to dose the gas flow conduit and allow the liquid flow conduit to be continuous by moving the piston to the pushed-in position from the normal position, and includes a seal member configured to be provided at either one of the cylinder and the piston, and isolate the gas flow conduit from an outside by elastically contacting a wall face of another one of the cylinder and the piston, when the piston is in the normal position or the pushed-in position, and leak means configured to be provided on the wall face of the other one, and open the gas flow conduit to the outside via a space between the cylinder and the piston by releasing contact of the seal member and the wall face of the other one, in a state where the piston is in a position that closes the liquid flow conduit and allows the gas flow conduit to be continuous, between the normal position and the pushed-in position.

DETAILED DESCRIPTION OF THE PREFERRED EMBODIMENT(S)

Hereinafter, the present invention will be described in accordance with an illustrated embodiment. In the respective drawings which will be used in the following explanation, respective components are sometimes shown with reduced scales caused to differ according to the respective components, in order to make the respective components have enough sizes to be recognized in the drawings. Consequently, in the present invention, numbers and quantities of the components illustrated in the drawings, shapes of the components, ratios of the sizes of the components and relative positional relationships of the respective components are not limited to illustrated forms.

Figure 1:
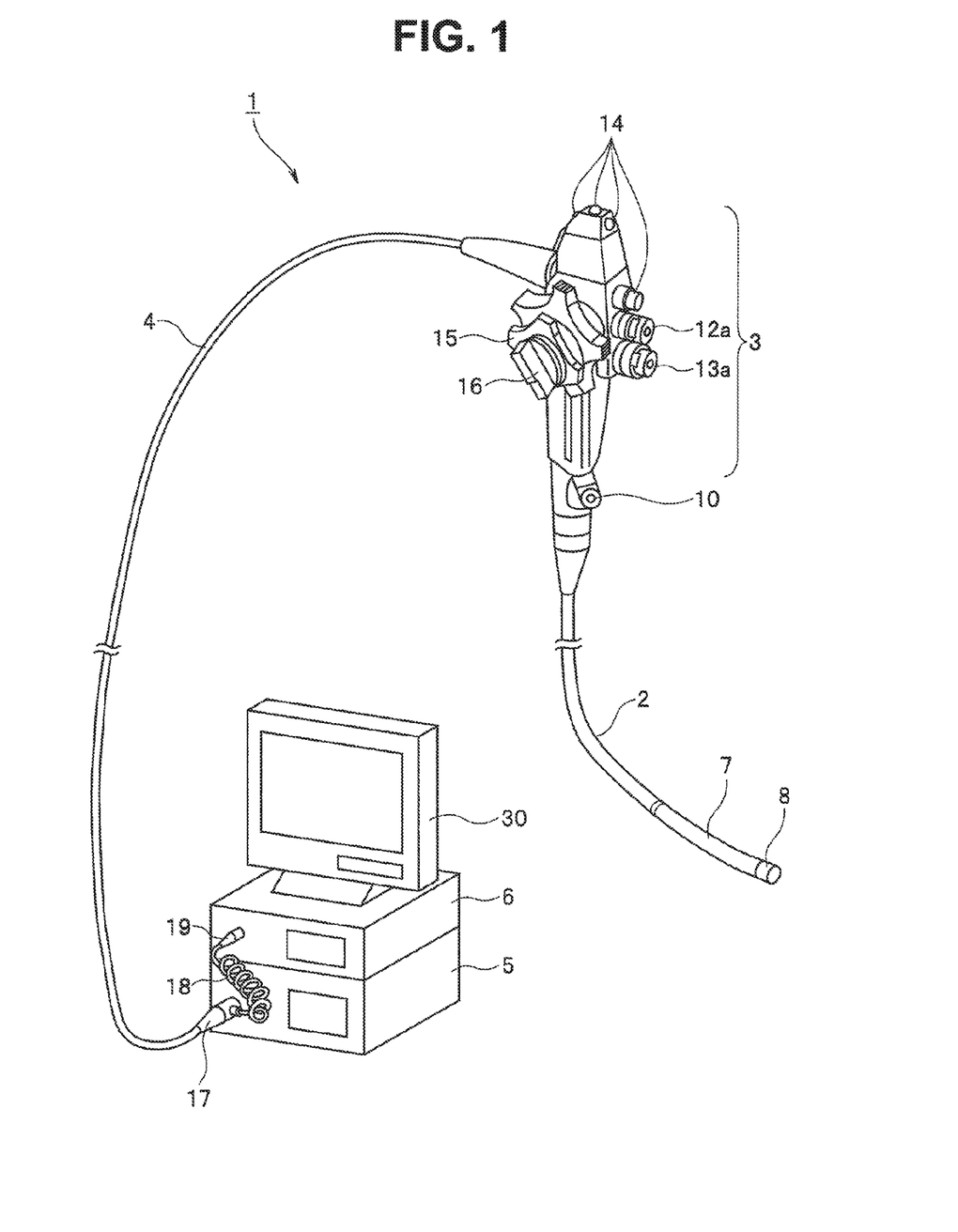
FIG. 1 is a schematic perspective view showing an entire configuration of an endoscope system including an endoscope conduit switching apparatus of one embodiment of the present invention.

First of all, a schematic configuration of an endoscope system including an endoscope conduit switching apparatus of one embodiment of the present invention will be described hereinafter with use of FIG. 1. FIG. 1 is a schematic perspective view showing an entire configuration of the endoscope system including the endoscope conduit switching apparatus of one embodiment of the present invention.

As shown in FIG. 1, the endoscope system is configured by an endoscope 1, a light source apparatus 5 which is an outside apparatus, a video processor 6, a display apparatus 30 and the like.

The above described endoscope 1 is configured by an elongated insertion portion 2, an operation portion 3 which a user (also referred to as an operator) grasps to perform an operation, a connection cord 4 for connecting the operation portion 3, and the light source apparatus 5 and the video processor 6 which are outside apparatuses and the like.

The insertion portion 2 is covered with a resin such as polyurethane, and a bending portion 7 which is bendable and covered with a soft elastic body is provided at a distal end portion of the insertion portion 2. A distal end rigid portion 8 is provided at a distal end of the bending portion 7. In the distal end rigid portion 8, an observation optical system, an image pickup device, an illumination optical system, an air/water feeding nozzle and the like (not illustrated) are provided. Further, in the distal end rigid portion 8, one opening of a forceps channel (not illustrated) which is inserted through an inside of the insertion portion 2 is provided. The other opening of the forceps channel (not illustrated) is provided connectively to a forceps opening portion 10 which is provided at the operation portion 3.

The operation portion 3 is provided with a plurality of various operation members such as an operation member 12a of a suction conduit switching apparatus which is operated at a time of suction being performed, an operation member 13a of an air/water feeding valve 13 (described in detail later) that is the air/water feeding conduit switching apparatus which is operated when air/water feeding is performed, and a plurality of remote switches 14 for performing various kinds of signal processing concerning a video signal which is obtained by the image pickup device.

Further, the operation portion 3 is provided with a plurality of angle knobs 15 made of a rigid resin. The bending portion 7 is configured to be able to be bent in a vertical and lateral directions by the angle knobs 15 (in plurality) being operated. At an upper portion of the angle knob 15, an operation member such as an engage lever 16 of a rigid resin which is used when the bending portion 7 is held in a bent and fixed state, and the bent and fixed state is released is provided.

The connection cord 4 is covered with a resin such as polyurethane, and a connector 17 which is formed of a rigid resin is attached to a distal end of the connection cord 4. The connector 17 is provided with a connection cord 18 which is extended from a side face, a water feeding tube (not illustrated) for performing water feeding by being connected to a water feeding tank (not illustrated; placed inside the light source apparatus 5), a suction port for performing suction by being connected to a suction pump not illustrated and the like. Note that to the above described water feeding tube, one end of a water feeding tube 72a which allows the water feeding tube and an inlet side water feeding conduit 39 of the air/water feeding valve 13 which will be described later to communicate with each other is connected. With the above components, in the connection cord 4, electric contacts, a light guide end portion and the like are provided at a distal end side.

Thereby, emission light from the light source apparatus 5 is configured to be emitted toward a front side from the illumination optical system in the distal end rigid portion 8 via the light guide which is inserted through and disposed in an inside of the endoscope by the connector 17 being connected to a connector receiving portion of the light source apparatus 5.

Further, at the distal end side of the connector 17, an air feeding tube (not illustrated) is provided to protrude substantially in parallel with the light guide end portion. Accordingly, pressurized air from an air feeding pump (not illustrated) which is provided in the light source apparatus 5 is configured to be fed to the above described air feeding tube when the connector 17 is connected to the connector receiving portion of the light source apparatus 5. Note that to the air feeding tube, one end of an air feeding tube 71a which allows the air feeding tube and an inlet side air feeding conduit 37 of the air/water feeding valve 13 which will be described later to communicate with each other is connected.

Further, in the connection cord 18 which is extended from the side face of the connector 17, a distal end connector 19 is connected to a connector receiving portion of the video processor 6. Thereby, an electric signal which is outputted from the image pickup device in the distal end rigid portion 8 of the endoscope 1 is configured to be transmitted to the video processor 6, subjected to predetermined signal processing in the video processor 6, and thereafter be able to be shown on a screen of the display apparatus 30 as an endoscopic image.

In the operation portion 3 of the above described endoscope 1 of the endoscope system configured as above, the air/water feeding valve 13 which is the endoscope conduit switching apparatus of the present embodiment is placed. Hereinafter, a detailed configuration of the air/water feeding valve 13 will be described on the basis of FIG. 2 to FIG. 4.

Figure 2:
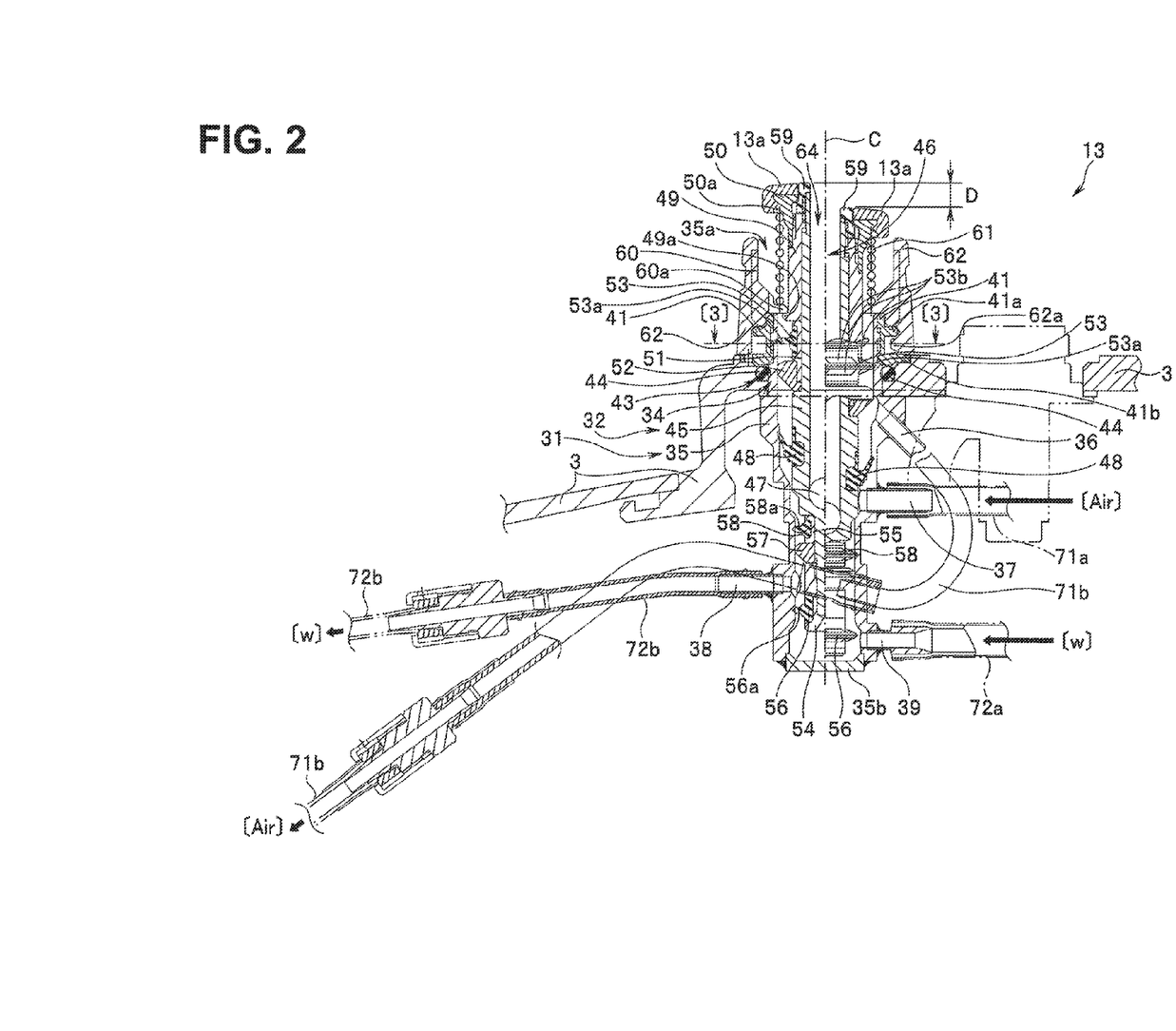
FIG. 2 is a vertical sectional view of the endoscope conduit switching apparatus (an air/water feeding valve) of the present embodiment which is included in the endoscope system in FIG. 1.
Figure 3:
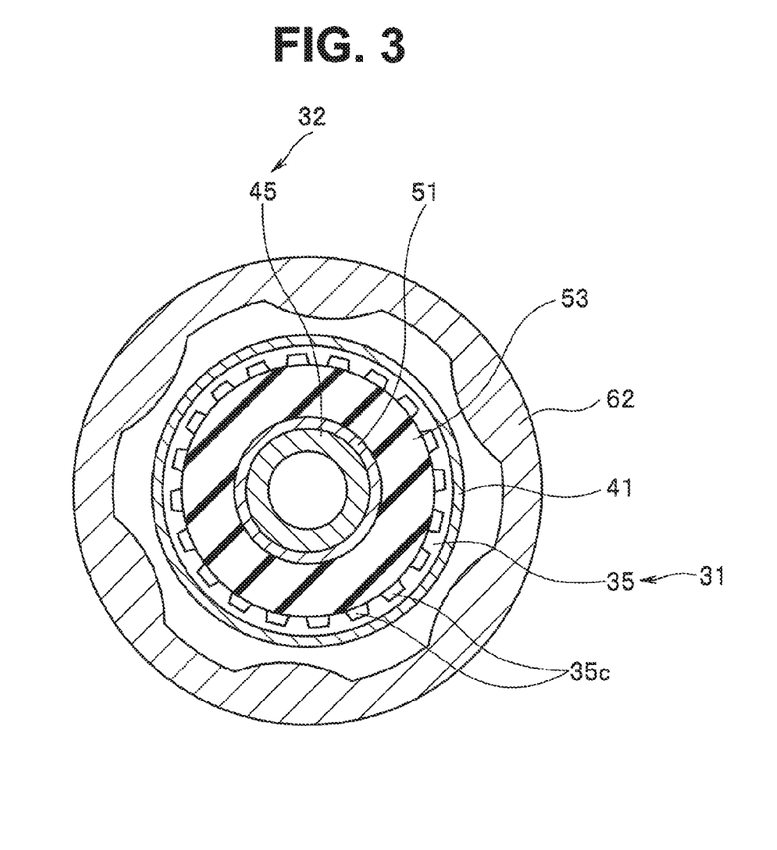
FIG. 3 is a cross sectional view taken along line [3] to [3] in FIG. 2.
Figure 4:
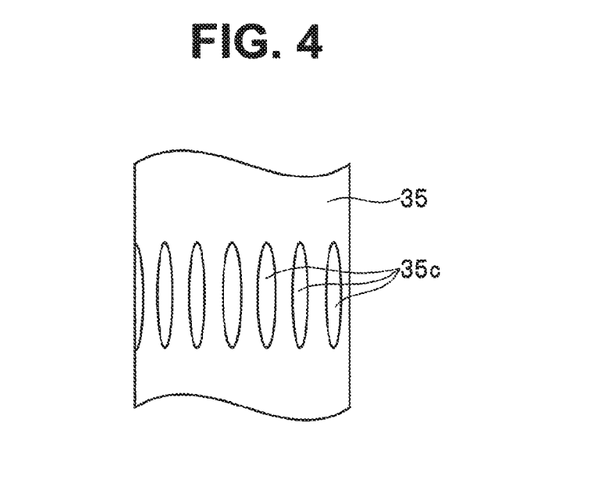
FIG. 4 is a view showing leak means (groove portions) which is formed on an inner wall face of a cylinder in the endoscope conduit switching apparatus (the air/water feeding valve) in FIG. 2.

FIG. 2 is a vertical sectional view of the endoscope conduit switching apparatus (the air/water feeding valve) of the present embodiment. Note that in FIG. 2, a left half part of a piston portion with an alternate long and short dash line as a center line C shows a normal state of the endoscope conduit switching apparatus, and a right half part of the same piston portion shows a state in which the air/water feeding button of the endoscope conduit switching apparatus is pushed down (a water feeding state). FIG. 3 is a cross sectional view taken along line [3] to [3] in FIG. 2. Further, FIG. 4 is a view showing leak means (groove portions) which is formed on an inner wall face of a cylinder in the endoscope conduit switching apparatus (the air/water feeding valve) of the present embodiment.

The air/water feeding valve 13 which is the endoscope conduit switching apparatus of the present embodiment is mainly configured by having a cylinder portion 31 to which a plurality of conduits provided in the endoscope 1 are connected, a piston portion 32 which is fitted and inserted into the cylinder portion 31 to be capable of advancing and retreating in an axial direction, and the like, and is a configuration unit which switches communication states of the above described plurality of conduits.

The cylinder portion 31 is fixed by using fixedly providing means such as screw fixing via a pipe sleeve member 41 which is mounted to a mounting hole 34 which is provided by being bored in a sheathing member of the operation portion 3. The piston portion 32 is fitted and inserted into the cylinder portion 31 slidably in an axial direction.

The cylinder portion 31 is mainly configured by a substantially cylindrical cylinder 35 of a metal having steps. The cylinder 35 has a through-hole which penetrates in an axial direction, and one opening 35a of both end openings of the through-hole opens outward, whereas the other opening is shielded by a lid member 35b.

In a side wall of the cylinder 35, an outlet side air feeding conduit 36, the inlet side air feeding conduit 37, an outlet side water feeding conduit 38 and the inlet side water feeding conduit 39 are provided in sequence, from a side of the above described opening 35a to a side of the above described lid member 35b.

Here, the outlet side air feeding conduit 36 is a site to which one end of an air feeding tube 71b that is inserted through the inside of the above described insertion portion 2 from the above described operation portion 3 to communicate with the above described air/water feeding nozzle (not illustrated) of the above described distal end id portion 8 is connected, and which functions as an outlet for gas which flows out from the air/water feeding valve 13. The outlet side air feeding conduit 36 configures a part of the gas flow conduit.

The inlet side air feeding conduit 37 is a site to which the other end of the air feeding tube 71a that is inserted through an inside of the above described connection cord 4 from the above described operation portion 3 to communicate with the above described air feeding pump (not illustrated) via an air feeding tube (not illustrated) of the above described connector 17 is connected, and which functions as an inlet for gas which flows into the air/water feeding valve 13. The inlet side air feeding conduit 37 configures a part of the gas flow conduit.

The outlet side water feeding conduit 38 is a site to which one end of a water feeding tube 72b that is inserted through the inside of the above described insertion portion 2 from the above described operation portion 3 to communicate with the above described air/water feeding nozzle (not illustrated) of the above described distal end rigid portion 8 is connected, and which functions as an outlet for a liquid which flows out from the air/water feeding valve 13. The outlet side water feeding conduit 38 configures a part of a liquid flow conduit.

The inlet side water feeding conduit 39 is a site to which the other end of the water feeding tube 72a that is inserted through the inside of the above described connection cord 4 from the above described operation portion 3 to communicate with the above described water feeding tank (not illustrated) via a water feeding tube (not illustrated) of the above described connector 17, and which functions as an inlet for a liquid which flows into the air/water feeding valve 13. The inlet side water feeding conduit 39 configures a part of the liquid flow conduit.

Note that although not illustrated, the other end of the air feeding tube 71b (refer to FIG. 2) which communicates with the above described outlet side air feeding conduit 36 and the other end of the water feeding tube 72b (refer to FIG. 2) which communicates with the above described outlet side water feeding conduit 38 are connected to the air/water feeding nozzle by the single tube (the common conduit portion) after joining each other via the branch tube which is provided in the insertion portion 2 of the endoscope 1. A configuration of the sites is similar to a configuration of an air/water feeding conduit in a conventional general endoscope.

As described above, the cylinder 35 is fixed to the sheathing member of the operation portion 3 via the pipe sleeve member 41. The above described pipe sleeve member 41 is formed by having two flange portions, that is, an upper flange 41a and a lower flange 41b.

When the cylinder 35 is in a state where the cylinder 35 is mounted and fixed to the sheathing member of the operation portion 3 via the pipe sleeve member 41, the lower flange 41b of the pipe sleeve member 41 compresses an O-ring 44 which is disposed to internally contact an annular groove portion 43 which is formed on an inner circumferential face of the mounting hole 34. By the configuration, the mounting hole 34 is hermetically sealed by the above described O-ring 44. Accordingly, a sealing structure is formed, which prevents gas and a liquid that enter the inside of the operation portion 3 from a mounting site of the cylinder 35 to the sheathing member of the operation portion 3.

The piston portion 32 is mainly configured by a substantially cylindrical piston main body 45 which is formed by using a material having rigidity such as a metal or a synthetic resin. A communication passage 46 which penetrates in an axial direction and forms a part of the gas flow conduit at a predetermined time is formed inside the piston main body 45. In a site near a lower end of the communication passage 46, a sideward opening portion 47 which opens to a direction (sideward) substantially orthogonal to the axial direction is formed.

At a site near to an upper side relative to the above described sideward opening portion 47, on an outer circumferential face of the piston main body 45, a valve body 48 which is formed of an elastic member is insert-molded into a circuit shape. The valve body 48 extends in an oblique direction toward an upper side from a side face of the piston main body 45, and a distal end of the valve body 48 is formed to abut on the inner wall face of the cylinder 35. By the shape like this, the gas flow conduit in a clearance formed between the outer circumferential face of the piston main body 45 and the inner circumferential face of the cylinder 35 is configured to allow a fluid (air) which flows upward from below to flow, but to prevent flow of the fluid (air) which flows downward from above.

Further, a removal prevention cylinder body 49 and a spring presser member 50 are screwed onto an upper end portion of the piston main body 45. Of the two components, the removal prevention cylinder body 49 is fixedly provided on an outer circumferential face of the upper end portion of the above described piston main body 45. The removal prevention cylinder body 49 has an outward flange portion 49a at a lower end portion, and is formed into a substantially cylindrical shape as a whole. The spring presser member 50 is fixedly provided onto an outer circumferential face of an upper end portion of the removal prevention cylinder body 49. The spring presser member 50 is formed by having an outward flange portion 50a at an upper end portion.

Further, at a lower side site of the above described removal prevention cylinder body 49, and on the outer circumferential face of the piston main body 45, a seal portion support member 51 is fixedly provided. At the seal portion support member 51, a seal member 53 is insert-molded in a circuiting manner on an outer circumferential face of the seal portion support member 51. A slider 52 is provided at a lower end side of the seal member 53.

In the seal member 53 of the seal portion support member 51, a strength reinforcing portion 53b is formed at each predetermined interval on a circumference at an inner circumferential side. Further, at an outer circumferential end portion of the seal member 53, a seal portion 53a which is formed to be deformable by elastically contacting the inner wall face of the cylinder 35 when the above described piston main body 45 is fitted and inserted to the inside of the cylinder 35.

In order to reduce slide resistance at a time of the seal member 53 sliding in the cylinder 35, the seal portion 53a of the seal member 53 needs to be made easily deformable when the seal portion 53a deforms by contacting the inner face of the cylinder 35. That is, a wall thickness of the seal portion 53a which is a contact portion of the seal member 53 with the cylinder 35 can be formed to be thin. However, if the wall thickness of the seal portion 53a is formed to be thin, water tightness and gas tightness between the cylinder 35 and the piston portion 32 are unlikely to be kept when the seal member 53 is excessively deformed, since the piston portion 32 of the air/water feeding valve 13 is movable in the axial direction (the vertical direction in FIG. 2). In that case, the air/water feeding valve 13 can be unable to perform a predetermined conduit switching function. Therefore, the seal member 53 is configured to be able to prevent excessive deformation of the seal member 53 to slide of the piston portion 32 and thereby prevent leakage of a liquid such as water, air and the like which is caused by excessive deformation, by being partially provided with the above described strength reinforcing portion 53b.

Note that although described later in detail, the above described seal member 53 is a seal member which is provided at either one (the piston portion 32 in the present embodiment) of the cylinder portion 31 and the piston portion 32 to isolate the gas flow conduit of the plurality of conduits from an outside, and elastically contacts a wall face of the other one (the cylinder portion 31 in the present embodiment), when the piston portion 32 is in a normal state (a state in FIG. 5).

A presser member 54 is placed at a lower end portion of the piston main body 45. A slider 57 is disposed at an upper side of the presser member 54, and a seal portion support member 55 is further disposed on a top surface of the slider 57. Further, at the above described presser member 54, a seal member 56 is insert-molded in a circuiting manner on an outer circumferential face of the presser member 54. At the seal portion support member 55, a seal member 58 is similarly insert-molded in a circuiting manner on an outer circumferential face.

The above described slider 57 is formed by a rigid resin member of PSU, PEEK or the like. The slider 57 may have a resin colored such as green that indicates being compatible with high pressure steam sterilization, for example. By coloring, a user (an operator) can easily recognize that the slider is compatible with high pressure steam sterilization.

The above described seal members 56 and 58 are respectively provided with strength reinforcing portions similarly to the above described seal member 53 (details not illustrated). Further, in the respective seal members 56 and 58, seal portions 56a and 58a similar to the above described seal portion 53a are formed at respective outer circumferential end portions. The seal portions 56a and 58a contact the inner wall face of the cylinder 35 and deform to be elastically brought into close contact with the inner wall face of the cylinder 35, when the above described piston main body 45 is fitted and inserted to the inside of the above described cylinder 35.

An enclosing member 62 is provided at an outer circumferential side of the pipe sleeve member 41. The enclosing member 62 is a substantially cylindrical member which is formed by using an insulating member, for example, and is provided to enclose an exposed portion of the air/water feeding valve 13 from the sheathing member of the operation portion 3. An inward flange portion 62a is formed at the enclosing member 62, and the inward flange portion 62a is engaged with the upper flange 41a of the above described pipe sleeve member 41.

A cylindrical piston stopper 60 is fixedly provided integrally on an inner circumferential face of an upper end side of the above described enclosing member 62. An inward flange portion 60a is formed at the piston stopper 60. The inward flange portion 60a locks a part of the piston portion 32, that is, the outward flange portion 49a of the removal prevention cylinder body 49 of the above described piston main body 45, at an undersurface side of the inward flange portion 60a, and thereby prevents the piston portion 32 from removing. Further, one end of an urging spring 61 which will be described later abuts on the inward flange portion 60a of the above described piston stopper 60, and the inward flange portion 60a becomes a site which holds the one end of the urging spring 61.

The urging spring 61 which is formed of a coil spring or the like is interposed between a top face side of the above described inward flange portion 60a of the above described piston stopper 60 and an undersurface side of the above described spring presser member 50. An urging force of the urging spring 61 acts in an extending direction to urge the spring presser member 50 upward in the axial direction, and the piston stopper 60 downward in the axial direction, respectively.

Accordingly, when the air/water feeding valve 13 is assembled and is in a normal state, the piston main body 45 is urged in a direction to remove from the cylinder 35 by the urging force of the urging spring 61. However, since the outward flange portion 49a of the removal prevention cylinder body 49 abuts on the inward flange portion 60a of the piston stopper 60, the piston main body 45 is locked so as not to remove from the cylinder 35.

Further, an identification pin 59 is screwed onto an upper end portion of the piston main body 45. Further, a finger contact member 13a is bonded and fixed to cover an upper end side and an outer circumferential portion of the above described spring presser member 50. In a central portion of the finger contact member 13a, a leak hole 64 which communicates with the above described communication passage 46 of the piston main body 45 and is an opening portion of the communication passage 46 is formed.

That is, the above described leak hole 64 is an opening which opens the conduit to the outside halfway through the communication passage 46 (the gas flow conduit). As will be described later, the gas flow conduit is configured to be completed by the user (the operator) closing the leak hole 64 with a finger or the like.

Further, the piston main body 45 is configured to open the liquid flow conduit by being pushed in against the urging force of the urging spring 61 in a state where the user (the operator) closes the above described leak hole 64 with a finger or the like. Reference sign D shown in FIG. 2 designates a stroke amount which shifts between the normal state of the piston main body 45 and a state where the piston main body 45 is pushed in.

A clearance with a predetermined space is structured to be always formed between an undersurface of the above described finger contact member 13a and an upper end of the above described enclosing member 62 (the opening 35a of the cylinder 35), in either case of a case where the above described piston portion 32 is in the normal state, or a case where the piston portion 32 is in the pushed-in state.

In the air/water feeding valve 13 which is the air/water feeding conduit switching apparatus of the present embodiment, on the inner circumferential face of the cylinder 35, a plurality of leak groove portions 35c which are disposed at predetermined intervals in a circumferential direction, for example, equidistantly, and are formed by having long axes in the axial direction are further provided in a site in approximately a middle of the inner circumferential face of the cylinder 35.

As for placement positions of the above described plurality of leak groove portions 35c, more specifically, the plurality of leak groove portions 35c are formed within a range in which the seal portion 53a of the above described seal member 53 moves when the cylinder 35 slides and moves in the axial direction. In that case, lengths in the axial direction of the respective leak groove portions 35c are set to be shorter than a range in the axial direction in which the seal portion 53a of the above described seal member 53 moves.

The plurality of leak groove portions 35c are leak means which is provided to cause a part of pressurized air which is fed from the air feeding pump (not illustrated) to flow out (leak) intentionally in a predetermined period on an occasion of the piston main body 45 sliding in the axial direction in the through-hole of the cylinder 35. Here, the predetermined time period in which air is intentionally caused to flow out (leak) is more specifically a predetermined time period between a time immediately after a water feeding operation is performed and water feeding operation is stopped, and a time immediately before the action is switched to a complete air feeding action.

Although details will be described later, the leak groove portion 35c which is the above described leak means is a component Which is provided on the wall face of the cylinder 35 of the cylinder portion 31, closes the liquid flow conduit Which extends from the inlet side water feeding conduit 39 to the outlet side water feeding conduit 38 in a middle of an action of releasing the state where the piston portion 32 is pushed in (the water feeding state), and thereafter opens the gas flow conduit to the outside.

Figure 6:
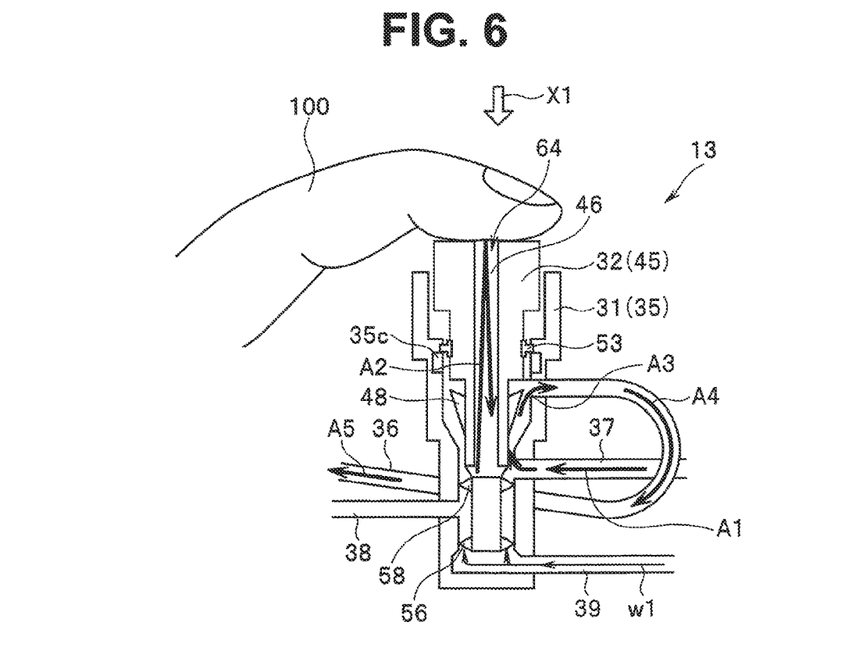
FIG. 6 is a view showing an air feeding state at a time of an air feeding operation being performed for the air/water feeding conduit switching apparatus (the air/water feeding valve) in the state of FIG. 5.
Figure 7:
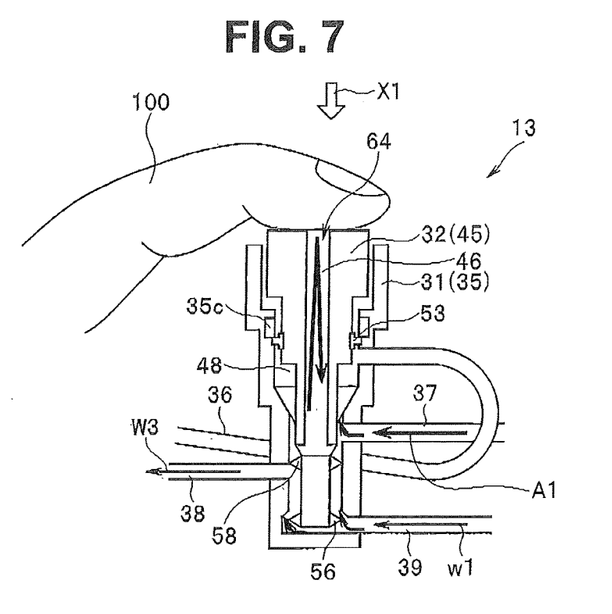
FIG. 7 is a view showing a water feeding state at a time of a water feeding operation being performed after the air feeding operation in FIG. 6 being performed.
Figure 8:
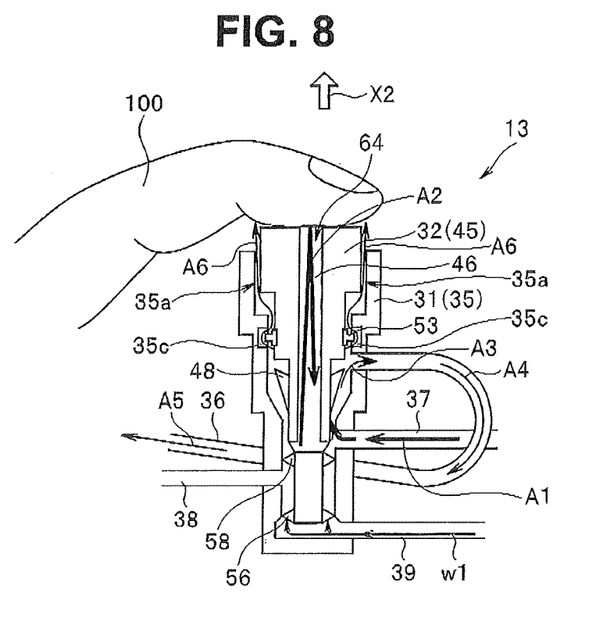
FIG. 8 is a view showing a situation in a course of a process of an operation of returning to the air feeding state again after the water feeding state in FIG. 7 is performed, and showing a leak state where air leaks from leak means (groove portions).

Hereinafter, an action of the air/water feeding operation which is performed by using the above described air/water feeding valve 13 which is the air/water feeding conduit switching apparatus of the present embodiment will be described with use of FIG. 5 to FIG. 8. FIG. 5 to FIG. 8 are schematic configuration views showing the action of the air/water feeding conduit switching apparatus (the air/water feeding valve) of the present embodiment. Of these drawings, FIG. 5 shows the normal state of the air/water feeding conduit switching apparatus (the air/water feeding valve). FIG. 6 shows an air feeding state at a time of performing an air feeding operation of the air/water feeding conduit switching apparatus (the air/water feeding valve). FIG. 7 shows a water feeding state at a time of performing a water feeding operation of the air/water feeding conduit switching apparatus (the air/water feeding valve) after the air feeding operation in FIG. 6. FIG. 8 shows a leak state where air leaks from the leak means (the groove portions), which is a situation in a middle of a process on an occasion of the air/water feeding conduit switching apparatus (the air/water feeding valve) being returned to the air feeding state again after the water feeding state in FIG. 7.

Figure 5:
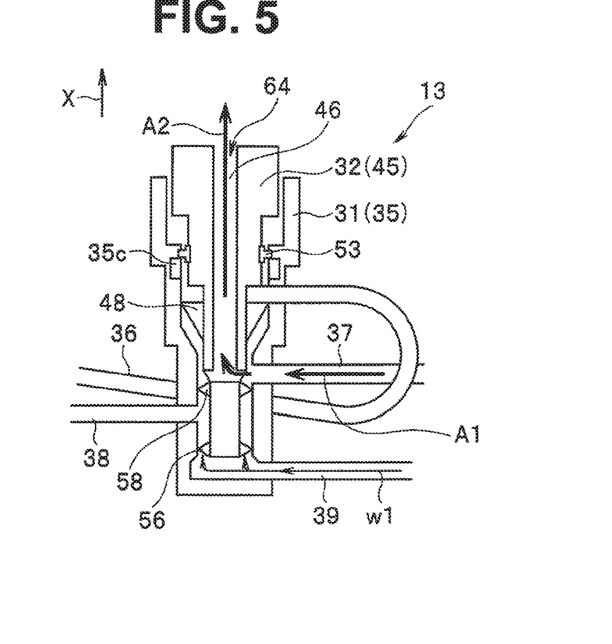
FIG. 5 is a schematic configuration view showing an action of the air/water feeding conduit switching apparatus (the air/water feeding valve) in FIG. 2, and is a view showing a normal state of the air/water feeding conduit switching apparatus (the air/water feeding valve)

First, when the above described air/water feeding valve 13 which is the air/water feeding conduit switching apparatus of the present embodiment is in the normal state, the piston portion 32 (the piston main body 45) is urged in an arrow X direction shown in FIG. 5 by the urging three of the urging spring 61, in the cylinder portion 31 (the cylinder 35), as shown in FIG. 5. At this time, the piston 45 is configured not to remove from the cylinder 35 by predetermined locking means (locking of the inward flange portion 60a of the piston stopper 60 and the outward flange portion 49a of the removal prevention cylinder body 49 of the piston main body 45).

When the air/water feeding valve 13 is in the normal state, the gas flow conduit in the clearance between the piston main body 45 and the cylinder 35 is sealed by abutment of (the seal portion 53a of) the seal member 53 and the inner wall face of the cylinder 35 to prevent outflow and entry of fluids (air, water and the like).

Further, when the air/water feeding valve 13 is in the normal state, the clearance (the gas flow conduit) is sealed by abutment of (the distal end of) the valve body 48 and the inner wall face of the cylinder 35 to prevent flow of the fluid (air).

Furthermore, when the air/water feeding valve 13 is in the normal state, the clearance (the liquid flow conduit) is sealed by abutment of (the seal portions 56a and 58a of) the seal members 56 and 58 and the inner wall face of the cylinder 35 to prevent flow of the fluid (water) from the inlet side water feeding conduit 39 at a lower part (refer to an arrow W1 in FIG. 5).

When the air/water feeding valve 13 is in the normal state, the fluid (air; refer to an arrow A1) which flows in from the inlet side air feeding conduit 37 passes through the communication passage 46 of the piston main body 45 to be caused to flow out to the outside from the leak hole 64 which is an opening portion of the communication passage 46 (refer to an arrow A2 in FIG. 5).

In this state, an air feeding operation is performed by the user (the operator) closing the leak hole 64 by using a finger or the like. A state where the air feeding operation is performed is the state shown in FIG. 6.

When the user (the operator) closes the leak hole 64 by the finger or the like as shown in FIG. 6, the fluid (air; an arrow W2) which is caused to flow out to the outside from the leak hole 64 in the normal state in FIG. 5 is prevented from flowing out to the outside by the finger or the like.

Thereby, the fluid (air; refer to an arrow A1) which flows in from the inlet side air feeding conduit 37 passes through the gas flow conduit in the clearance between the piston main body 45 and the cylinder 35 to flow in a direction of the valve body 48. At this time, the fluid (air) is pressurized, and therefore pushes up (the distal end of) the valve body 48 to flow out to the outlet side air feeding conduit 36 via the air feeding conduit (refer to arrows A3, A4 and A5 in FIG. 6). Here, as the valve body 48 receives flow of the fluid (air) from the inlet side air feeding conduit 37 at the lower part while the valve body 48 seals the clearance by the distal end of the valve body 48 abutting on the inner wall face of the cylinder 35, flow of the fluid (air) from above is prevented.

In this state, the user (the operator) pushes down the piston portion 32 in a direction of an arrow X1 in FIG. 6 while the user closes the leak hole 64 by using the finger or the like, whereby a water feeding operation is performed. A state in which the water feeding operation is performed is the state shown in FIG. 7.

As described above, when the user (the operator) pushes down the piston portion 32 in the direction of the arrow X1 by the finger or the like, the valve body 48 and the cylinder 35 are in close contact with each other, and outflow, to the air feeding conduit, of the fluid (air; refer to an arrow A1) which flows in from the inlet side air feeding conduit 37 is prevented, as shown in FIG. 7.

At the same time, abutment of (the seal portion 56a of) the seal member 56 and the inner wall face of the cylinder 35 is released, and the liquid flow conduit in the clearance between the cylinder 35 and the piston main body 45 communicates with the outlet side water feeding conduit 38. Thereby, the fluid (water) from the inlet side water feeding conduit 39 flows out from the outlet side water feeding conduit 38 (refer to an arrow W3 in FIG. 7).

Note that in this state, the clearance is sealed by abutment of (the seal portion 58a of) the seal member 58 and the inner wall face of the cylinder 35, and therefore, the fluid (water) from the inlet side water feeding conduit 39 is prevented from flowing into a clearance portion at an upper part from the outlet side water feeding conduit 38.

When the user (the operator) reduces the force to push down of the finger or the like while the user closes the leak hole 64 by using the finger in this state, the piston portion 32 is pushed up in a direction of an arrow X2 in FIG. 8 by the urging force of the urging spring 61. Thereby, the water feeding operation is switched to the air feeding operation. A state of a process in progress of the switching operation is the state shown in FIG. 8.

As described above, when the piston portion 32 is pushed up in the direction of the arrow X2, (the seal portion 56a of) the seal member 56 and the inner wall face of the cylinder 35 abut on each other again in the process, the clearance is sealed to prevent flow of the fluid (water) from the inlet side water feeding conduit 39 (refer to an arrow W1 in FIG. 8).

At this time, the close contact of the valve body 48 and the cylinder 35 is released, and outflow, to the air feeding conduit, of the fluid (air; refer to an arrow A1) which flows in from the inlet side air feeding conduit 37 is restarted. At the same time, (the seal portion 53a) of the seal member 53 passes through positions corresponding to the plurality of leak groove portions 35c. In the time period, a part of the fluid (air) which flows in from the inlet side air feeding conduit 37 flows out (leaks) to the outside from the opening 35a of the cylinder 35 through the clearance between the cylinder 35 and the piston main body 45 via the above described plurality of leak groove portions 35c (refer to an arrow A6 in FIG. 8). Thereby, a pressure of the fluid (air; refer to an arrow A5 in FIG. 8), which flows out to the outlet side air feeding conduit 36 through the air feeding conduit (refer to arrows A3 and A4 in FIG. 8), of the fluid (air; refer to the arrow A1) which flows in from the inlet side air feeding conduit 37, is decreased.

As described above, the fluid (air; refer to the arrow A5 in FIG. 8) which flows out from the outlet side air feeding conduit 36 is configured to flow out to the air/water feeding nozzle via the air feeding tube 71b (refer to FIG. 2) and the branch tube (not illustrated) in the insertion portion 2 of the above described endoscope 1.

Accordingly, the decompressed fluid (air) which flows to the air/water feeding nozzle from the outlet side air feeding conduit 36 does not have enough pressure to cause a residual liquid (water), which remains in the tube (the common conduit portion) in a space from the above described branch tube to the air/water feeding nozzle, to reach the observation window, and therefore the residual liquid (water) is discharged from a distal end of the air/water feeding nozzle without reaching the outer surface of the observation window. After the above described residual liquid (water) is discharged, it is necessary to increase the pressure of the fluid (air) which flows to the air/water feeding nozzle from the outlet side air feeding conduit 36 immediately, and dry the outer surface of the observation window quickly. Decompression can be performed at predetermined timing for only a predetermined time period, by the strength of the spring 61, the positions and the lengths in the axial direction of the leak groove portions 35c being adjusted.

As described above, according to the above described one embodiment, the plurality of leak groove portions 35c which are formed by having long axes in the axial direction are formed in the predetermined positions on the inner circumferential face of the cylinder 35 in the air/water feeding valve 13, that is, the site within the range in which the seal portion 53a of the seal member 53 moves when the cylinder 35 slides and moves in the axial direction, and the outflow fluid (air) from the outlet side air feeding conduit 36 is configured to be decompressed by a part of the fluid (air) which flows out from the outlet side air feeding conduit 36 being caused to flow out to the outside via the above described plurality of leak groove portions 35c for only a predetermined time period, in the process in which the water feeding operation is switched to the air feeding operation after the water feeding operation is performed.

Accordingly, the liquid (water) which remains in the common conduit portion when water feeding is switched to air feeding can be thereby pushed out from the air/water feeding nozzle without being caused to reach the observation window. Thereafter, the state is configured to be switched to the air feeding state, and therefore the reliable water feeding state and air feeding state can be always ensured.

Further, according to the present embodiment, by only the simple configuration change in which the leak groove portions 35c are only provided as the leak means, the configuration which performs decompression in the gas flow conduit by leaking the fluid (air) to the outside intentionally at the predetermined timing for only the predetermined time period in the operation process can be realized without changing the conventional operability and without forcing the user (the operator) to perform a special operation or the like.

Note that in the air/water feeding valve 13 which is the air/water feeding conduit switching apparatus of the above described one embodiment, a form of the leak means which is provided on the inner circumferential face of the cylinder 35 of the cylinder portion 31 is not limited to the form of the aforementioned plurality of leak groove portions 35c.

In the normal case, the seal portion 53a of the seal member 53 at the side of the piston main body 45 which reciprocates and slides in the axial direction of the cylinder 35 slides and moves in the axial direction while the seal portion 53a is brought into pressure contact with the inner circumferential face of the cylinder 35. Accordingly, if the leak means is formed into a shape having a step in the axial direction, the seal. portion 53a is caught at the time of the seal member 53 sliding, and smooth slide cannot be obtained.

Therefore, as the other forms of the leak means, various forms are conceivable, such as a circumferential groove which has a smooth inclined face in the axial direction and has a section in a substantially V-shape, or a circumferential groove which has smooth inclined faces at both ends in the axial direction with a bottom face connecting both the inclined faces formed by having a predetermined length in the axial direction.

The present invention is not limited to the aforementioned embodiment, and it is needless to say that various modifications and applications can be carried out within the range without departing from the gist of the present invention. Further, the above described embodiment includes the inventions in various stages, and various inventions can be extracted by arbitrary combinations in the plurality of components which are disclosed. For example, even when some components are deleted from all the components shown in the above described one embodiment, if the problem to be solved by the invention can be solved, and the effect of the invention can be obtained, the configuration from which the components are deleted can be extracted as the invention. Furthermore, the components throughout different embodiments may be arbitrarily combined.

INDUSTRIAL APPLICABILITY

The present invention can be applied to not only an endoscope control apparatus in the medical field but also an endoscope control apparatus in the industrial field.

What is claimed is:

1. An endoscope conduit switching apparatus configured to have a cylinder to which a plurality of conduits provided in an endoscope and including a gas flow conduit and a liquid flow conduit are connected, a piston that is fitted and inserted into the cylinder to be capable of advancing and retreating, and is moved between a normal position and a pushed-in position where the piston is pushed inward of the cylinder from the normal position, and an urging member that urges the piston toward the normal position, and switch communication states of the plurality of conduits so as to close the gas flow conduit and allow the liquid flow conduit to be continuous by moving the piston to the pushed-in position from the normal position, comprising:
    a seal member configured to be provided at either one of the cylinder and the piston, and isolate the gas flow conduit from an outside by elastically contacting a wall face of another one of the cylinder and the piston, when the piston is in the normal position or the pushed-in position; and
    leak means configured to be provided on the wall face of the other one, and open the gas flow conduit to the outside via a space between the cylinder and the piston by releasing contact of the seal member and the wall face of the other one, in a state where the piston is in a position that closes the liquid flow conduit and allows the gas flow conduit to be continuous, between the normal position and the pushed-in position.

2. The endoscope conduit switching apparatus according to claim 1,
    wherein the leak means is a groove that is provided on the wall face of the other one.

3. The endoscope conduit switching apparatus according to claim 1,
    wherein the piston comprises an opening where the gas flow conduit is opened to the outside halfway through the gas flow conduit, and the gas flow conduit is completed by the opening being closed by an operator.

* * * * *

UNITED STATES PATENT AND TRADEMARK OFFICE
CERTIFICATE OF CORRECTION

PATENT NO. : 10,034,603 B2
APPLICATION NO. : 15/266725
DATED : July 31, 2018
INVENTOR(S) : Naomi Matsuo Page 1 of 1

It is certified that error appears in the above-identified patent and that said Letters Patent is hereby corrected as shown below:

Column 14, Lines 12-48 should read:
1. An endoscope conduit switching apparatus comprising:
a cylinder connected to a plurality of conduits provided in an endoscope, the plurality of conduits including a gas flow conduit and a liquid flow conduit;
a piston fitted and inserted into the cylinder to be capable of advancing and retreating, the piston being movable between a normal position and a pushed-in position where the piston is pushed inward of the cylinder from the normal position;
an urging member that urges the piston toward the normal position, and switches communication states of the plurality of conduits so as to close the gas flow conduit and allow the liquid flow conduit to be continuous by moving the piston to the pushed-in position from the normal position;
a seal member provided at one of the cylinder and the piston, the seal member isolating the gas flow conduit from an outside by elastically contacting a wall face of an other one of the cylinder and the piston, when the piston is in the normal position or the pushed-in position; and
a leak groove provided on the wall face of the other one of the cylinder and the piston, the leak groove opening the gas flow conduit to the outside via a space between the cylinder and the piston by releasing contact of the seal member and the wall face of the other one of the cylinder and the piston, in a state where the piston is in a position that closes the liquid flow conduit and allows the gas flow conduit to be continuous, between the normal position and the pushed-in position.
2. The endoscope conduit switching apparatus according to claim 1, wherein the piston comprises an opening for allowing an end portion of the gas flow conduit to be opened to the outside, the gas flow conduit being completed by the opening being closed.
3. The endoscope conduit switching apparatus according to claim 1, wherein the piston opens the liquid flow conduit by being pushed in, in a state where the opening is configured to be closed.

Signed and Sealed this
Eleventh Day of December, 2018

Andrei Iancu
*Director of the United States Patent and Trademark Office*